United States Patent
Biasutto et al.

(10) Patent No.: US 11,920,132 B2
(45) Date of Patent: *Mar. 5, 2024

(54) OLIGONUCLEOTIDE THERAPY FOR LEBER CONGENITAL AMAUROSIS

(71) Applicant: ProQR Therapeutics II B.V., Leiden (NL)

(72) Inventors: Patricia Coromoto Biasutto, The Hague (NL); Hee Lam Chan, Den Hagg (NL)

(73) Assignee: ProQR Therapeutics II B.V., Leiden (NL)

(*) Notice: Subject to any disclaimer, the term of this patent is extended or adjusted under 35 U.S.C. 154(b) by 4 days.

This patent is subject to a terminal disclaimer.

(21) Appl. No.: 17/144,728

(22) Filed: Jan. 8, 2021

(65) Prior Publication Data

US 2021/0139905 A1  May 13, 2021

Related U.S. Application Data

(63) Continuation of application No. 16/576,853, filed on Sep. 20, 2019, now Pat. No. 10,889,817, which is a continuation of application No. 15/551,026, filed as application No. PCT/EP2016/054164 on Feb. 26, 2016, now Pat. No. 10,421,963.

(30) Foreign Application Priority Data

Feb. 27, 2015 (GB) ..................................... 1503408

(51) Int. Cl.
*C12N 15/11* (2006.01)
*A61K 31/7125* (2006.01)
*C12N 15/113* (2010.01)

(52) U.S. Cl.
CPC ........ *C12N 15/113* (2013.01); *A61K 31/7125* (2013.01); *C12N 2310/11* (2013.01); *C12N 2310/315* (2013.01); *C12N 2310/346* (2013.01); *C12N 2320/33* (2013.01); *C12N 2330/51* (2013.01)

(58) Field of Classification Search
CPC .............. C12N 15/113; C12N 2310/11; C12N 2310/315; C12N 2310/346; C12N 2320/33; A61K 31/7125
See application file for complete search history.

(56) References Cited

U.S. PATENT DOCUMENTS

| | | | |
|---|---|---|---|
| 5,139,941 A | 8/1992 | Muzyczka et al. | |
| 6,001,652 A * | 12/1999 | Monia ................ | C12N 15/1135 435/375 |
| 6,531,546 B2 | 3/2003 | Oka et al. | |
| 8,524,880 B2 | 9/2013 | Wilton et al. | |
| 10,421,963 B2 | 9/2019 | Biasutto et al. | |
| 10,889,817 B2 | 1/2021 | Biasutto et al. | |
| 2005/0233455 A1 | 10/2005 | Damha et al. | |
| 2009/0269755 A1 | 10/2009 | Aartsma-Rus et al. | |
| 2012/0108654 A1 | 5/2012 | Campochiaro | |

FOREIGN PATENT DOCUMENTS

| | | |
|---|---|---|
| EP | 2425814 | 3/2012 |
| WO | WO 2005086768 | 9/2005 |
| WO | WO 2006000057 | 1/2006 |
| WO | WO 2008029790 | 3/2008 |
| WO | WO 2009121536 | 10/2009 |
| WO | WO 2012168435 | 12/2012 |
| WO | WO 2013036105 | 3/2013 |
| WO | WO 2015004133 | 1/2015 |
| WO | WO 2016034680 | 3/2016 |

OTHER PUBLICATIONS

Popplewell et al., "Comparative analysis of antisense oligonucleotide sequences targeting exon 53 of the human DMD gene: Implications for future clinical trials," Neuromuscular Disorders, Feb. 2010, 20(2):102-110.
Aartsma-Rus et al., "Guidelines for Antisense Oligonucleotide Design and Insight Into Splice-modulating Mechanisms," Mol Ther., Mar. 2009, 17(3):548-553.
Baye et al. (2011) "The N-terminal region of centrosomal protein 290 (CEP290) restores vision in a zebrafish model of human blindness," Hum. Mol. Genet., 20(8):1467-77.
Chiorini et al. (1999) "Cloning and characterization of adeno-associated virus type 5," J. Viral., 73(2):1309-19.
Cideciyan et al. (2007) "Centrosomal-ciliary gene CEP290/NPHP6 mutations result in blindness with unexpected sparing of photoreceptors and visual brain: implications for therapy of Leber congenital amaurosis," Hum. Mutat., 28(11):1074-83.
Collin et al. (2011) "Antisense oligonucleotide (AON)-based therapy for CEP290 associated LCA," Poster presented at ARVO Annual Meeting (May 3, 2011 ).
Collin et al., "Antisense Oligonucleotide (AON)-based Therapy for Leber Congenital Amaurosis Caused by at Frequent Mutation in CEP290", Molecular Therapy-Nucleic Acids, 2012, 1(3):e14.
Database EMBL [Online], "Sequence 410497 from Patent EP2213738.", XP002758305, retrieved from EBI accession No. EM_PAT:HD533781, Database accession No. HD533781 sequence, 2010.
Database EMBL [Online], "Sequence 478723 from Patent EP1572962." XP002758304, retrieved from EBI accession No. EM_PAT:JD497699, Database accession No. JD497699 sequence, 2015.

(Continued)

*Primary Examiner* — Ekaterina Poliakova-Georgantas
(74) *Attorney, Agent, or Firm* — Fish & Richardson P.C.

(57) ABSTRACT

Antisense oligonucleotides target the mutation in intron 26 of the CEP290 gene and reduce inclusion of the aberrant exon into the CEP290 mRNA. The oligonucleotides include no more than 3 consecutive guanosines, have no more than 60% guanosine nucleobases, include at most one CpG sequence, and/or do not have the potential to form a hairpin comprising 3 or more consecutive complementary base pairs.

2 Claims, 3 Drawing Sheets

Specification includes a Sequence Listing.

(56) References Cited

OTHER PUBLICATIONS

Database EMBL [Online], "Sequence 854314 from Patent EP2213738." XP002758303, retrieved from EBI accession No. EM_PAT:HD977598, Database accession No. HD977598 sequence, 2010.

Den Hollander et al. (2006) "Mutations in the CEP29O (NPHP6) gene are a frequent cause of Leber conqenital amaurosis," Am. J. Hum. Genet. 79(3):556-61.

Den Hollander, et al., (2008), "Leber congenital amaurosis: genes, proteins and disease mechanisms," Prog Retin. Eye Res., 27(4):391-419.

Dorn et al. (2008) "Clinical application of CpG-, non-CpG-, and antisense oligodeoxynucleotides as immunomodulators," Curr. Opin. Mol. Ther., 10(1):10-20.

Egholm et al. (1993) "PNA hybridizes to complementary oligonucleotides obeying the Watson-Crick hydroqen-bondinq rules," Nature, 365(6446):566-8.

Estrada-Cuzcano et al. (2011) "IQCB1 mutations in patients with leber congenital amaurosis," Invest. Ophthalmol. Vis. Sci., 52(2):834-9.

Garanto et al., "AAV-mediated antisense oligonucleotide delivery is an effective therapeutic approach for CEP290-associated LCA", Human Gene Therapy, 2014, vol. 25, No. 11, P074, p. ABO.

Gerard et al., "AON-mediated Exon Skipping Restores Ciliation in Fibroblasts Harboring the Common Leber Congenital Amaurosis CEP290 Mutation", Molecular Therapy-Nucleic Acids, 2012, 1(6):e29.

Gorman et al. (1998) "Stable alteration of pre-mRNA splicing patterns by modified U7 small nuclear RNAs," Proc. Natl. Acad. Sci. USA, 95(9):4929-34.

Govindaraju et al. (2005) "Backbone-extended pyrrolidine peptide nucleic acids (bepPNA): design, synthesis and DNA/RNA binding studies," Chem. Commun. (Camb.), 4:495-7.

International Search Report and Written Opinion in PCT Appln. No. PCT/EP2016/054164, dated Jun. 15, 2016, 13 pages.

Koenekoop et al. (2007) "Genetic testing for retinal dystrophies and dysfunctions: benefits, dilemmas and solutions," Clin. Exp. Qphthalmol., 35(5):473-85.

Koenekoop et al. (2007) "Leber Congenital Amaurosis: Ciliary Proteins on the Move," Ophthalmic Genetics, 28(3): 111-112.

Littink et al. (2010) "A novel nonsense mutation in CEP29O induces exon skipping and leads to a relatively mild retinal phenotvPe," Invest. Ophthalmol. Vis. Sci., 51 (7):3646-52.

Morita et al. (2001) "2'-0,4'-C-ethylene-bridged nucleic acids (ENA) with nuclease-resistance and high affinity for RNA," Nucleic Acids Res. Suppl., 1 :241-2.

Nielsen et al. (1991) "Sequence-selective recognition of DNA by strand displacement with a thymine-substituted polyamide," Science, 254(5037): 1497-500.

Perrault et al. (2007) "Spectrum of NPHP6/CEP29O mutations in Leber congenital amaurosis and delineation of the associated phenotype," Hum. Mutat., 28(4):416.

Stone (2007) "Leber congenital amaurosis—a model for efficient genetic testing of heterogeneous disorders: LXIV Edward Jackson Memorial Lecture," Am. J. Ophthalmol., 144(6):791-811.

Suter et al. (1999) "Double-target antisense U7 snRNAs promote efficient skipping of an aberrant exon in three human beta-thalassemic mutations," Hum. Mol. Genet., 8(13):2415-23.

Veltrop et al. (2014) "Antisense-mediated exon skipping: taking advantage of a trick from Mother Nature to treat rare genetic diseases," Exp. Cell Res., 325(1):50-5.

* cited by examiner

FIGURE 1

3'-ACGGTTATCCCTATCCATACTCTATaAGTGTTAATGTTGACCCCGGTCCACGCCACCGAGTGTAGACATTAGGGTCGTGAAATCCTC...

| | | | |
|---|---|---|---|
| AONP26 | GGAUAGGUAUGAGAUAc | UGCGGUGGCUCACAUCU | AONP20 |
| AONP24 | GGUAUGAGAUAcUCACA | GCGGUGGCUCACAUCUG | AONP2 |
| AONP23 | cUCACAAUUACAACUGG | GGUGGCUCACAUCUGUA | AONP3 |
| | | UGGCUCACAUCUGUAAU | AONP19 |
| | | GGCUCACAUCUGUAAUC | AONP4 |

WO2012/168435:

cugggccaggugcgguggcucacaucugua gggauagguaugagauaCucacaau gguaugagauaCucacaauuac gguaugagauaCucacaauuacaacuggggc

WO2013/036105:

taatcccagcactttaggag gggccaggtgcggtgg aactggggccaggtgcg tacaactggggccaggtg aCtcacaattacaactgggg

...CGGCTCCGCCCACCTAGTGCTCAAGTCCTCTAGCTGTGGTAGGACCGATTGTTCCACTTTGGGGTAGAGAT-5'

| | |
|---|---|
| AONP11 | UCAGGAGAUCGACACCA |
| AONP12 | CACGAGUUCAGGAGAUC |
| AONP13 | GGUGGAUCACGAGUUCA |

WO2012/168435:

ccgaggcggguggaucacgag

OLIGONUCLEOTIDE THERAPY FOR LEBER CONGENITAL AMAUROSIS

CROSS-REFERENCE TO RELATED APPLICATIONS

This application is a continuation of U.S. application Ser. No. 16/576,853, filed on Sep. 20, 2019, now U.S. Pat. No. 10,889,817, which is a continuation of U.S. application Ser. No. 15/551,026, filed on Aug. 14, 2017, now U.S. Pat. No. 10,421,963, which is a § 371 national phase of International Application No. PCT/EP2016/054164, filed on Feb. 26, 2016, which claims priority from U.K. Patent Application No. 1503408.5 filed on 27 Feb. 2015. The complete contents of each of which are incorporated herein by reference for all purposes.

FIELD OF THE INVENTION

The present invention relates to the field of oligonucleotides and their use for the treatment of disease. In particular, the invention pertains to novel antisense oligonucleotides that may be used in the treatment of Leber Congenital Amaurosis.

BACKGROUND OF THE INVENTION

Leber Congenital Amaurosis (LCA) is the most common form of congenital childhood blindness with an estimated prevalence of approximately 1 in 50,000 newborns, worldwide (Koenekoop et al., 2007; Stone, 2007). It is accompanied by retinal dystrophy. The onset of disease symptoms is as early as the first months or years in life (Leber, T., 1869). Genetically, LCA is a heterogeneous disease, with fifteen genes identified to date in which mutations are causative for LCA (den Hollander et al., 2008; Estrada-Cuzcano et al., 2011). The most frequently mutated LCA gene is CEP290, a gene located on the Q arm of chromosome 12, coding for Centrosomal Protein 290 which has an important role in centrosome and cilia development. Mutations in the CEP290 gene are responsible for about 15% of all LCA cases (Stone, 2007; den Hollander, 2008; den Hollander, 2006; Perrault et al., 2007).

The by far most frequently occurring CEP290 mutation, associated with retinal dystrophy, especially in European countries and in the US, is a change in intron 26 of the CEP290 gene (c.2991+1655A>G) (Stone, 2007; den Hollander et al., 2006; Perrault et al., 2007; Liitink et al., 2010). This mutation creates a cryptic splice donor site in intron 26 which results in the inclusion of an aberrant exon of 128 bp in the mutant CEP290 mRNA, and inserts a premature stop codon (p.C998X) (see FIG. 1). In patients with this mutation, the wild-type transcript that lacks the aberrant exon is still produced, explaining the hypomorphic nature of this mutation (Estrada-Cuzcano et al., 2011).

WO2013/036105 (Stichting Katholieke Universiteit Nijmegen) and WO2012/168435 (Inserm et al.) disclose antisense oligonucleotides for the treatment or delay of LCA, targeting this intronic mutation in CEP290.

SUMMARY OF THE INVENTION

Although the antisense oligonucleotides disclosed in WO2013/036105 and WO2012/168435 reduce the selection of the cryptic splice site associated with the mutation, thereby reducing the generation of spliced CEP290 mRNAs containing the aberrant 128 bp exon sequence (also referred to as "exon skipping"), the oligonucleotides themselves have certain limitations from a manufacturability and/or immunological point of view, which may limit their usability in a human therapeutic setting. It is therefore an object of the present invention to provide novel antisense oligonucleotides that target the mutation in intron 26 of the CEP290 gene, that do not suffer from some of the drawbacks of oligonucleotides of the prior art, while effectively reducing the inclusion of the aberrant exon into the CEP290 mRNA.

Accordingly, the invention provides an oligonucleotide capable of reducing splice site selection of an aberrant splice site associated with the c.2991+1655A>G mutation in intron 26 of the human CEP290 gene, when said gene is expressed in a human cell;

characterized in that the oligonucleotide's sequence has at least one of properties (a) to (d):
(a) it includes no more than 3 consecutive guanosines;
(b) it has no more than 60% guanosine nucleobases;
(c) it includes at most one CpG sequence; and/or
(d) it does not have the potential to form a hairpin comprising 3 or more consecutive complementary base pairs, provided that the oligonucleotide (i) does not consist of SEQ ID NO: 16 and/or (ii) consists of 21 or fewer nucleotides, and preferably consists of 20 or fewer nucleotides.

Without wishing to be bound by theory, the inventors believe that the oligonucleotide's complementarity to human CEP290 pre-mRNA means that it is capable of binding to it under physiological conditions in a region affecting selection of the aberrant splice site, and upon binding to said region it reduces selection of the splice site by the cell's splicing machinery.

Oligonucleotides can possess combinations of two, three, or even four of features (a) to (d) defined above. Such combinations are described in more detail below.

The oligonucleotides are generally shorter than 30 nucleotides e.g. ≤25nt, ≤21nt, ≤20nt. They can be 16-19nt long e.g. 17nt long.

Specific oligonucleotide sequences of interest are SEQ ID NOs: 2-12.

The oligonucleotides preferably contain chemical modifications when compared to natural RNA e.g. a phosphorothioate backbone, 2'-O-lower alkyl-modified ribose moieties, etc.

The oligonucleotides can be provided directly to a cell, or can be provided indirectly by in situ transcription e.g. from a viral vector. However they are supplied, they can be used to provide a therapeutic effect in vivo for treating a human carrying in its genome the (c. 2991+1655A>G) mutation in intron 26 of the CEP290 gene.

DESCRIPTION OF THE FIGURES

FIG. 1: sense strand of the human genome (SEQ ID NO: 30) including the 128 bp cryptic exon (underlined; SEQ ID NO: 1) plus 30 bp downstream. The location of antisense oligonucleotides according to the invention are also shown (SEQ ID NOs: 2-12) as well as AONs of the prior art (SEQ ID NOs: 13-22). The c.2991+1655A>G mutation, downstream of the cryptic exon, is shown in lower case in the genome sequence.

DETAILED DESCRIPTION OF THE INVENTION

Figure 2:
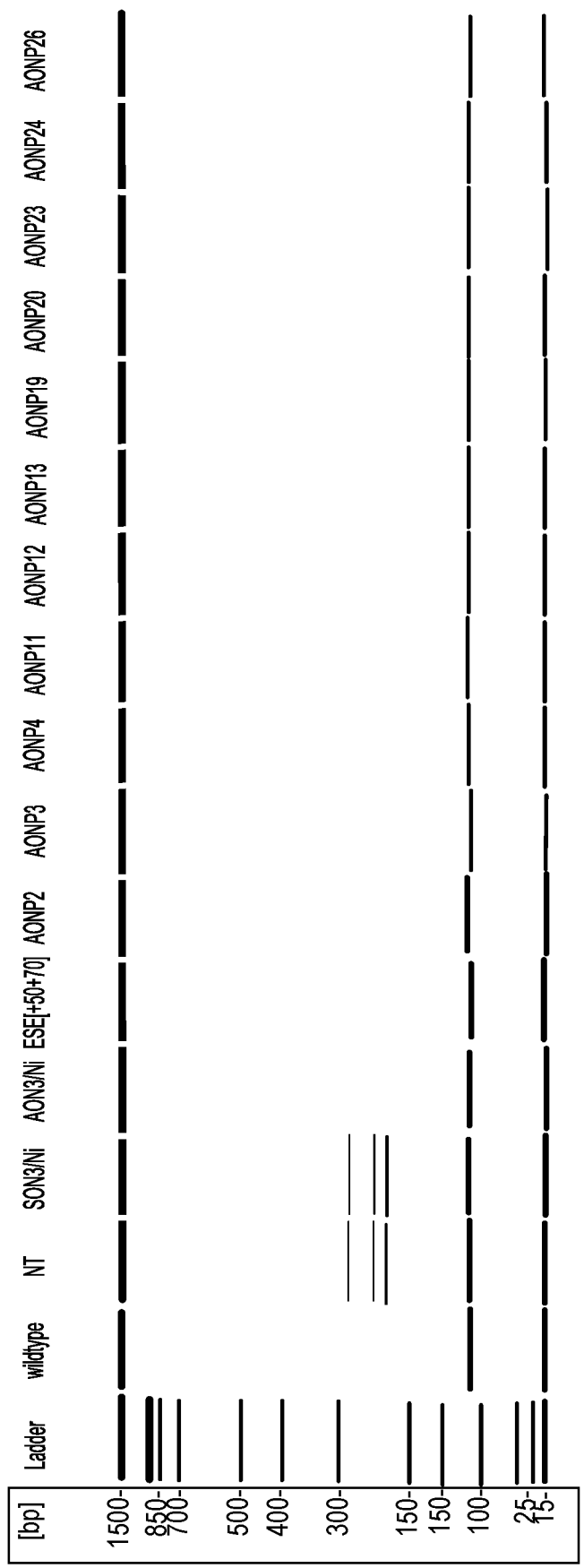
FIG. 2: CEP290 mRNA splicing profiles of non-treated patient cells (NT), patient cells treated with non-complementary (sense) oligonucleotides (SON-3; SEQ ID NO: 29) or complementary antisense oligonucleotides according to the invention (AONP) compared to prior art AONs. Wild type fragment corresponds to a band that migrates at approximately 109 bp while the mutated fragment corresponds to a band that migrates at approximately 237 bp. The fragments migrating above the 237 bp fragment are believed to be other forms of aberrant splicing. The healthy control exhibits only a wild type profile while the patient shows presence of both wild type and mutated fragments. The designated oligonucleotides can efficiently induce exon skipping of the targeted mutant sequence and therefore restore a wild type mRNA profile.
Figure 3:
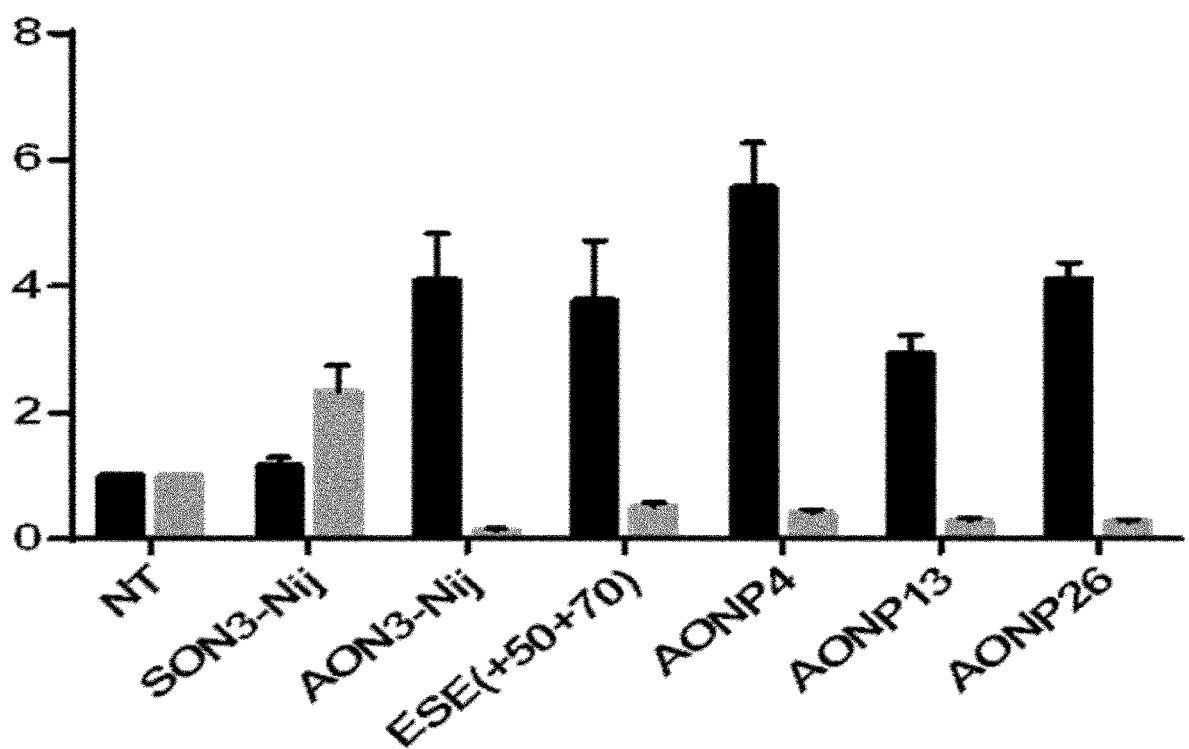
FIG. 3: Expression of CEP290 mRNA in patient samples after treatment with AONs shown on the x-axis. Fold change (y-axis) was calculated using the Comparative Ct method. Levels of wild type mRNA (black bars) and mutant mRNA (grey bars) were compared to the non-treated sample. The error bars represent the standard deviation of the mean. Statistical analysis of the difference between levels of the wild type transcript in non-treated patient samples vs. treated patient samples was carried out using a paired t-test. Results show a significant difference ($p<0.05$) of levels of the wild type transcript after antisense oligonucleotide treatment but not after treatment with same sense oligonucleotide. (SON-3 p=0.2507, AONP4 p=0.0002, AONP13 p=0.0001, AONP26 p<0.0001, AON-3 p=0.0034, ESE(+50+70) p=0.0193)

Surprisingly, it has now been demonstrated that antisense oligonucleotides (AONs) can be designed, that are able to block or reduce aberrant splicing of the cryptic 128 bp exon in the CEP290 pre-mRNA and which meet the requirements for therapeutic use in humans.

Thus AONs according to the invention are not only functional, but equally importantly, and contrary to the exon skipping AONs of the prior art are devoid of sequences that are prone to aggregate or multiplex formation, such as repetitive G's (3 or more G's, including 4 or more G's, also referred to as G-tetrads or quadruplexes) which cause problems with purification (impurities) and analytics after bulk manufacturing, solubility (for example due to stacking of the G-tetrads), biodistribution, cellular uptake, immunogenicity and/or overall loss of function.

The AONs according to the invention do not contain more than 60%, more preferably not more than 50%, still more preferably not more than 40% guanosine nucleotides.

Moreover, the AONs of the invention contain not more than one CpG sequence, preferably no CpG sequence, known to induce the human immune system through a TLR9 mediated reaction.

In addition, contrary to some exon skipping AONs disclosed in the prior art, the AONs of the invention do not contain long inverted repeats (sequences that can create hairpins or other double stranded structures), which may pose problems with purification and analytics and are associated with immunogenicity, reduced cellular uptake and/or overall loss of function.

Accordingly, in a first aspect the present invention provides an oligonucleotide capable of reducing splice site selection of an aberrant splice site associated with the c.2991+1655A>G mutation in intron 26 of the human CEP290 gene when said gene is expressed in a human cell, wherein the oligonucleotide is complementary to and capable of binding under physiological conditions to the human CEP290 pre-mRNA in a region affecting selection of the aberrant splice site and upon binding to said region reduces selection of said splice site by the splicing machinery in said cell;

characterized in that the oligonucleotide's sequence has at least one of properties (a) to (d):
(a) it includes no more than 3 consecutive guanosines;
(b) it has no more than 60% guanosine nucleobases;
(c) it includes at most one CpG sequence; and/or
(d) it does not have the potential to form a hairpin comprising 3 or more consecutive complementary base pairs,
provided that the oligonucleotide does not consist of SEQ ID NO: 16.

According to property (a), the oligonucleotide may include a GpG dinucleotide sequence, but there are no more than 3 consecutive guanosine nucleobases in the sequence. Thus guanosine tetrads are absent, as are longer stretches of guanosine repeats.

According to property (b), the oligonucleotide may include guanosine nucleobases, but no more than 60% of the individual nucleobases in the oligonucleotide can be guanosine. Ideally no more than 50% of the nucleobases are guanosine, and preferably no more than 40%.

According to property (c), the oligonucleotide may include one CpG dinucleotide sequence, but no more. In some embodiments the oligonucleotide includes no CpG dinucleotide sequence.

According to property (d), the oligonucleotide omits sequences of 3 nucleotides or more which are self-complementary and which can thus hybridize to each other within the oligonucleotide to form hairpins of 3 base pairs or more (intramolecular duplexes), or can hybridize to each other in different oligonucleotides to form intermolecular duplexes.

It is also preferred that an oligonucleotide's sequence should have no more than 3 consecutive cytdidine nucleobases. More generally, in some embodiments an oligonucleotide's sequence does not include any stretch of 3 or more consecutive identical nucleobases e.g. it does not include any of ApApA, CpCpC, GpGpG, or UpUpU trinucleotides.

In a second aspect the invention provides an oligonucleotide capable of reducing splice site selection of an aberrant splice site associated with the c.2991+1655A>G mutation in intron 26 of the human CEP290 gene when said gene is expressed in a human cell, wherein the oligonucleotide is complementary to and capable of binding under physiological conditions to the human CEP290 pre-mRNA in a region affecting selection of the aberrant splice site and upon binding to said sequence reduces selection of said splice site by the splicing machinery in said cell;

characterized in that the oligonucleotide consists of 21 or fewer nucleotides (preferably 20 or fewer) and its sequence has at least one of properties (a) to (d):
(a) it includes no more than 3 consecutive guanosines;
(b) it has no more than 60% guanosine nucleobases;
(c) it includes at most one CpG sequence; and/or
(d) it does not have the potential to form a hairpin comprising 3 or more consecutive complementary base pairs.

In addition, a third aspect of the invention provides an oligonucleotide capable of reducing splice site selection of an aberrant splice site associated with the c.2991+1655A>G mutation in intron 26 of the human CEP290 gene when said gene is expressed in a human cell, wherein the 5' or 3' terminal nucleotide of the oligonucleotide is a cytidine at the position which is antisense to the c.2991+1655A>G mutation. This oligonucleotide can also have at least one of properties (a) to (d).

In a fourth aspect the invention provides an oligonucleotide capable of reducing splice site selection of an aberrant splice site associated with the c.2991+1655A>G mutation in intron 26 of the human CEP290 gene when said gene is expressed in a human cell, wherein the oligonucleotide includes a sequence of at least 10 nucleotides which is complementary to at least a portion of the sequence 5'-atggtgtcgatctcctgaactcgtga-3' (SEQ ID NO: 31; nucleotides 31-56 of SEQ ID NO: 1). This oligonucleotide can thus anneal to any portion of SEQ ID NO: 31, but will always include at least one nucleotide which is complementary to the central 8-mer thereof, namely 5'-atctcctg-3' (SEQ ID NO: 32) which is a potential splicing enhancer sequence. AONP11, 12 & 13 are examples of such oligonucleotides, each of which includes at least one nucleotide from the central 8-mer 5'-caggagat-3' (SEQ ID NO: 36; see FIG. 1). This oligonucleotide can also have at least one of properties (a) to (d).

Ideally an oligonucleotide of the invention has more than one of said properties (a) to (d). For instance, it can have properties: (a) & (b); (a) & (c); (a) & (d); (b) & (c); (b) & (d); (a), (b) & (c); (a), (b) & (d); (a), (c) & (d); or all four of (a), (b), (c) & (d).

The following table provides the AONs of the prior art, highlighting (in bold) the features that are to be avoided in order to prevent problems with manufacturing, purification, analytics, aggregate formation, immunogenicity and/or loss of function associated therewith:

| Prior art sequence | AON name &/or SEQ ID in prior art | SEQ ID |
|---|---|---|
| cuggggccaggugcgguggu cacaucugua | ESE(+90+120); WO2012/ 168435 SEQ ID NO: 1 | 13 |
| ccgaggcggguggaucacgag | ESE(+50+70); WO2012/ 168435 SEQ ID NO: 2 | 15 |
| gggauagguaugagauacuca caau | H26D(+7-18); WO2012/ 168435 SEQ ID NO: 4 | 14 |
| gguaugagauacucacaauuac | H26D(+10-11); WO2012/ 168435 SEQ ID NO: 5 | 16 |
| gguaugagauacucacaauuac aacuggggc | H26D(+19-11); WO2012/ 168435 SEQ ID NO: 6 | 17 |
| gggccaggtgcggtgg | AON-2; WO2013/036105 SEQ ID NO: 10 | 19 |
| aactggggccaggtgcg | AON-3; WO2013/036105 SEQ ID NO: 11 | 20 |
| tacaactggggccaggtg | AON-4; WO2013/036105 SEQ ID NO: 12 | 21 |

Preferred AONs according to the invention are provided in the table below: AONP2 (SEQ ID NO: 2), AONP3 (SEQ ID NO: 3), AONP4 (SEQ ID NO: 4), AONP11 (SEQ ID NO: 5), AONP12 (SEQ ID NO: 6), AONP13 (SEQ ID NO: 7), AONP19 (SEQ ID NO: 8), AONP20 (SEQ ID NO: 9), AONP23 (SEQ ID NO: 10), AONP24 (SEQ ID NO: 11) and AONP26 (SEQ ID NO: 12):

| AON | Oligo Sequence | SEQ ID NO: |
|---|---|---|
| AONP2 | GCGGUGGCUCACAUCUG | 2 |
| AONP3 | GGUGGCUCACAUCUGUA | 3 |
| AONP4 | GGCUCACAUCUGUAAUC | 4 |
| AONP11 | UCAGGAGAUCGACACCA | 5 |
| AONP12 | CACGAGUUCAGGAGAUC | 6 |
| AONP13 | GGUGGAUCACGAGUUCA | 7 |
| AONP19 | UGGCUCACAUCUGUAAU | 8 |
| AONP20 | UGCGGUGGCUCACAUCU | 9 |
| AONP23 | CUCACAAUUACAACUGG | 10 |
| AONP24 | GGUAUGAGAUACUCACA | 11 |
| AONP26 | GGAUAGGUAUGAGAUAC | 12 |

In the AONs in the table substantially all ribose moieties are 2'-O-methylated and substantially all internucleosidic linkages are phosphorothioates.

More preferred AONs according to the invention are those having the sequence of AONP4, AONP13 and AONP26, still more preferred having substantially all 2'-O-methyl-ribose moieties, and substantially all phosphorothioate internucleosidic linkages.

In all embodiments of the present invention, the terms "modulating splicing" and "exon skipping" are synonymous. In respect of CEP290, "modulating splicing" or "exon skipping" are to be construed as the exclusion of the aberrant 128 nucleotide exon (SEQ. ID NO: 1, or allelic forms thereof) from the CEP290 mRNA (see FIG. 1). The term exon skipping is herein defined as the induction within a cell of a mature mRNA that does not contain a particular exon that would be present in the mature mRNA without exon skipping. Exon skipping is achieved by providing a cell expressing the pre-mRNA of said mature mRNA with a molecule capable of interfering with sequences such as, for example, the (cryptic) splice donor or (cryptic) splice acceptor sequence required for allowing the biochemical process of splicing, or with a molecule that is capable of interfering with an exon inclusion signal required for recognition of a stretch of nucleotides as an exon to be included in the mature mRNA; such molecules are herein referred to as exon skipping molecules.

The term pre-mRNA refers to a non-processed or partly processed precursor mRNA that is synthesized from a DNA template in cell by transcription.

The term "antisense oligonucleotide" is understood to refer to a nucleotide sequence which is complementary to a target nucleotide sequence in a pre-mRNA molecule, hnRNA (heterogeneous nuclear RNA) or mRNA molecule, so that it is capable of annealing with its corresponding target sequence.

The term "complementary" as used herein includes "fully complementary" and "substantially complementary", meaning there will usually be a degree of complementarity between the oligonucleotide and its corresponding target sequence of more than 80%, preferably more than 85%, still more preferably more than 90%, most preferably more than 95%. For example, for an oligonucleotide of 20 nucleotides in length with one mismatch between its sequence and its target sequence, the degree of complementarity is 95%.

The degree of complementarity of the antisense sequence is preferably such that a molecule comprising the antisense sequence can anneal to the target nucleotide sequence in the RNA molecule under physiological conditions, thereby facilitating exon skipping. It is well known to a person having ordinary skill in the art, that certain mismatches are more permissible than others, because certain mismatches have less effect on the strength of binding, as expressed in terms of melting temperature or Tm, between AON and target sequence, than others. Certain non-complementary basepairs may form wobbles that disrupt the overall binding to a lesser extent than true mismatches. The length of the AON also plays a role in the strength of binding, longer AONs having higher melting temperatures as a rule than shorter AONs, and the G/C content of an oligonucleotide is also a factor that determines the strength of binding, the higher the G/C content the higher the melting temperature for any given length. Certain chemical modifications of the nucleobases or the sugar-phosphate backbone, as contemplated by the present invention, may also influence the strength of binding, such that the degree of complementarity is only one factor to be taken into account when designing an oligonucleotide according to the invention.

The presence of a CpG or multitude (two or more) of CpGs in an oligonucleotide is usually associated with an increased immunogenicity of said oligonucleotide (Dorn and Kippenberger, 2008). This increased immunogenicity is undesired since it may induce damage of the tissue to be treated, i.e. the eye.

The invention allows designing an oligonucleotide with acceptable RNA binding kinetics and/or thermodynamic properties. The RNA binding kinetics and/or thermodynamic properties are at least in part determined by the melting temperature of an oligonucleotide (Tm; calculated with the oligonucleotide properties calculator (www.unc.edu/~cail/biotool/oligo/index.html) for single stranded RNA using the basic Tm and the nearest neighbor models), and/or the free energy of the AON-target exon complex (using RNA structure version 4.5). If a Tm is too high, the oligonucleotide is expected to be less specific. An acceptable Tm and free energy depend on the sequence of the oligonucleotide, the chemistry of the backbone (phosphodiester, phosphorothioate, phosphoramidate, peptide-nucleic acid, etc.), the nature of the sugar moiety (ribose, deoxyribose, substituted ribose, intramolecular bridge) and chemical modification of the nucleobase. Therefore, the range of Tm can vary widely.

The present invention provides a method for designing an AON according to the invention by microwalking the entire cryptic exon with oligo's of a particular length. The length of the oligo selected by the present inventors was 17 nucleotides, but a different length is also possible. It is preferred to have a length that is long enough to allow for a stable interaction with the target RNA and specificity for the target sequence but not longer than necessary, as longer oligonucleotides are more expensive to manufacture and are more complex from an analytical point of view. Subsequently, the entire cryptic exon or a part thereof may be probed for efficient exon skipping molecules, by making a series of overlapping oligonucleotides that are tested in an in vitro assay for their efficacy of exon skipping as exemplified in the examples. In an alternative approach, the cryptic exon is searched for potential splicing enhancing motifs and a range of AONs is designed directed to those motifs. The AONs that establish a satisfactory exon skipping efficacy are then further selected on the basis of the manufacturability, immunogenicity and other usability criteria provided herein.

The opposite strategy is also possible. In accordance with this strategy, the oligo's are first designed based on the manufacturability, immunogenicity and other usability criteria provided by the present invention, and are then tested for exon skipping efficacy. A functional activity of said oligonucleotide is preferably to induce the skipping of the aberrant 128 nucleotide CEP290 exon (SEQ ID NO: 1) to a certain extent and/or at least in part decreasing the production of an aberrant CEP290 mRNA, thereby increasing the production of wt CEP290 mRNA. In a preferred embodiment, an oligonucleotide is said to induce skipping of the aberrant 128 nucleotide CEP290 exon (SEQ ID NO: 1), when the aberrant 128 nucleotide CEP290 exon (SEQ ID NO: 1) skipping percentage as measured by real-time quantitative RT-PCR analysis (is at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or at least 99%.

The skipping percentage (or efficiency of splice site skipping) may be calculated by determining the concentration of wild-type band amplified, divided by the concentration of the mutant band amplified, after a given number of PCR cycles, times 100%, for any given primer set, provided the number of cycles is such that the amplification is still in the exponential phase.

Preferred AONs according to the invention are those showing a skipping percentage of more than 70% in AON-treated cells compared to non-treated cells, more preferably more than 80%, still more preferably more than 90%, as measured by RT-PCR analysis.

Preferably, an AON according to the invention, which comprises a sequence that is complementary to a nucleotide sequence as shown in SEQ ID NO: 1 is such that the complementary part is at least 80%, more preferably at least 90%, still more preferably at least 95%, most 100% complementary to the target sequence. The length of said complementary part of said oligonucleotide is preferably at least 10, 11, 12, 13, 14, 15, 16, 17, 18, 19, 20, 21, 22, 23, 24, 25, 26, 27, 28, 29 or 30 nucleotides. According to a more preferred embodiment the length of the complementary part is between about 12 and about 25 nucleotides, more preferably between 14 and about 20 nucleotides, most preferably 16, 17, 18, 19 or 20 nucleotides. Preferably, the length of the complementary part of the oligonucleotide is the same as the length of the oligonucleotide, meaning there are no 5' or 3' ends of the oligo that do not form a basepair with the target RNA. Thus a preferred length for an oligonucleotide of the invention is 30 nucleotides or less e.g. <25, <20, or 16-19 nucleotides.

It is thus not absolutely required that all the bases in the region of complementarity are capable of pairing with bases in the opposing strand. For instance, when designing the oligonucleotide one may want to incorporate for instance a residue that does not base pair with the base on the complementary strand. Mismatches may, to some extent, be allowed, if under the circumstances in the cell, the stretch of nucleotides is sufficiently capable of hybridizing to the complementary part. In this context, "sufficiently" means that that the AONs according to the invention are capable of inducing exon skipping of the cryptic 128 bp exon. Skipping the targeted (cryptic) exon may conveniently be assessed by RT-PCR. The complementary regions are preferably designed such that, when combined, they are specific for the exon in the pre-mRNA. Such specificity may be created with various lengths of complementary regions as this depends on the actual sequences in other (pre-)mRNA molecules in the system. The risk that the oligonucleotide also will be able to hybridize to one or more other pre-mRNA molecules decreases with increasing size of the oligonucleotide. It is clear that oligonucleotides comprising mismatches in the region of complementarity but that retain the capacity to hybridize and/or bind to the targeted region(s) in the pre-mRNA, can be used in the present invention. However, preferably at least the complementary parts do not comprise such mismatches as these typically have a higher efficiency and a higher specificity, than oligonucleotides having such mismatches in one or more complementary regions. It is thought, that higher hybridization strengths, (i.e. increasing number of interactions with the opposing strand) are favorable in increasing the efficiency of the process of interfering with the splicing machinery of the system. Preferably, the complementarity is from 90% to 100%. In general this allows for 1 or 2 mismatch(es) in an oligonucleotide of 20 nucleotides or 1, 2, 3 or 4 mismatches in an oligonucleotide of 40 nucleotides, or 1, 2, 3, 4, 5 or 6 mismatches in an oligonucleotide of 60 nucleotides, etc.

An exon skipping molecule of the invention is preferably an (antisense) oligonucleotide, which is complementary to SEQ ID NO: 1.

In those embodiments of the present invention wherein an exon skipping molecule comprises or consists of an antisense oligonucleotide that binds to or is complementary to at least the part of SEQ ID NO: 1 that comprises the c.2991+1655A>G mutation, said exon skipping molecule preferably comprises a "C" nucleotide on the position complementary to the mutated "G" nucleotide in SEQ ID NO: 1.

In certain embodiments, the invention provides an exon skipping molecule comprising or preferably consisting of an antisense oligonucleotide selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12.

In a more preferred embodiment, the invention provides an exon skipping molecule comprising or preferably consisting of the antisense oligonucleotide SEQ ID NO: 4, SEQ ID NO: 7 or SEQ ID NO: 11. It was found that these AONs are very efficient in modulating splicing of the aberrant 128 nucleotide CEP290 exon, while they do not containing G-tetrads, a guanosine nucleobase composition of more than 60% (50% or 40%), (more than) one CpG sequence, or sequences that can form hairpin structures comprising more than 3 consecutive basepairs.

In some embodiments an oligonucleotide of the invention does not consist of SEQ ID NO: 16. In some embodiments an oligonucleotide of the invention does not include SEQ ID NO: 16. In some embodiments an oligonucleotide of the invention is not a RNA which consists of sequence gcgguggcucacaucuguaauc, (SEQ ID NO: 33)

gggcgcggguggcucacaucugua, (SEQ ID NO: 34)
or cgcggguggcucacaucugu. (SEQ ID NO: 35)

An exon skipping molecule according to the invention may contain one of more DNA residues (consequently a RNA "u" residue will be a "t" residue as DNA counterpart), or one or more RNA residues, and/or one or more nucleotide analogues or equivalents, as will be further detailed herein below. SEQ ID NOs: 2 to 12 are RNA sequences, but the invention also encompasses each of these sequences in DNA form, and also DNA/RNA hybrids of these sequences.

It is preferred that an exon skipping molecule of the invention comprises one or more residues that are modified to increase nuclease resistance, and/or to increase the affinity of the antisense oligonucleotide for the target sequence. Therefore, in a preferred embodiment, the antisense nucleotide sequence comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells. A recent report demonstrated triplex formation by a morpholino oligonucleotide and, because of the non-ionic backbone, these studies showed that the morpholino oligonucleotide was capable of triplex formation in the absence of magnesium.

It is further preferred that the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al. (1993) Nature 365, 566-568).

A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; methoxyethoxy; -dimethylaminooxyethoxy; and -dimethylaminoethoxyethoxy. The sugar moiety can be a furanose or derivative thereof, or a deoxyfuranose or derivative thereof, preferably ribose or derivative thereof, or deoxyribose or derivative of. A preferred derivatized sugar moiety comprises a Locked Nucleic Acid (LNA), in which the $2^1$-carbon atom is linked to the 3' or 4' carbon atom of the sugar ring thereby forming a bicyclic sugar moiety. A preferred LNA comprises 2'-O,4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target RNA.

In another embodiment, a nucleotide analogue or equivalent of the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art.

It is understood by a skilled person that it is not necessary for all positions in an antisense oligonucleotide to be modified uniformly. In addition, more than one of the aforementioned analogues or equivalents may be incorporated in a single antisense oligonucleotide or even at a single position within an antisense oligonucleotide. In certain embodiments, an antisense oligonucleotide of the invention has at least two different types of analogues or equivalents.

According to another embodiment AONs according to the invention comprise a 2'-O (preferably lower) alkyl phosphorothioate antisense oligonucleotide, such as 2'-O-methyl modified ribose (RNA), 2'-O-methoxyethyl modified ribose, 2'-O-ethyl modified ribose, 2'-O-propyl modified ribose, and/or substituted derivatives of these modifications such as halogenated derivatives.

An effective and preferred antisense oligonucleotide according to the invention comprises 2'-O-methyl modified ribose moieties with a phosphorothioate backbone, preferably wherein substantially all ribose moieties are 2'-O-methyl and substantially all internucleosidic linkages are phosphorothioate linkages.

It will also be understood by a skilled person that different antisense oligonucleotides can be combined for efficiently skipping of the aberrant 128 nucleotide exon of CEP290. A combination of two antisense oligonucleotides may be used in a method of the invention, such as two antisense oligonucleotides, three different antisense oligonucleotides, four different antisense oligonucleotides, or five different antisense oligonucleotides targeting the same or different regions of the cryptic exon (FIG. 1).

An antisense oligonucleotide can be linked to a moiety that enhances uptake of the antisense oligonucleotide in cells, preferably retina cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a camelid single domain antigen-binding domain.

An exon skipping molecule according to the invention may be indirectly administrated using suitable means known in the art. When the exon skipping molecule is an oligonucleotide, it may for example be provided to an individual or a cell, tissue or organ of said individual in the form of an expression vector wherein the expression vector encodes a transcript comprising said oligonucleotide. The expression vector is preferably introduced into a cell, tissue, organ or individual via a gene delivery vehicle. In a preferred embodiment, there is provided a viral-based expression vector comprising an expression cassette or a transcription cassette that drives expression or transcription of an exon skipping molecule as identified herein. Accordingly, the present invention provides a viral vector expressing an exon skipping molecule according to the invention when placed under conditions conducive to expression of the exon skipping molecule. A cell can be provided with an exon skipping molecule capable of interfering with essential sequences that result in highly efficient skipping of the aberrant 128 nucleotide CEP290 exon by plasmid-derived antisense oligonucleotide expression or viral expression provided by adenovirus- or adeno-associated virus-based vectors. Expression may be driven by a polymerase III promoter, such as a U1, a U6, or a U7 RNA promoter. A preferred delivery vehicle is a viral vector such as an adeno-associated virus vector (AAV), or a retroviral vector such as a lentivirus vector and the like. Also, plasmids, artificial chromosomes, plasmids usable for targeted homologous recombination and integration in the human genome of cells may be suitably applied for delivery of an oligonucleotide as defined herein. Preferred for the current invention are those vectors wherein transcription is driven from PolIII promoters, and/or wherein transcripts are in the form fusions with U1 or U7 transcripts, which yield good results for delivering small transcripts. It is within the skill of the artisan to design suitable transcripts. Preferred are PolIII driven transcripts. Preferably, in the form of a fusion transcript with an U1 or U7 transcript. Such fusions may be generated as described (Gorman L et al., 1998 or Suter D et al., 1999).

One preferred antisense oligonucleotide expression system is an adenovirus associated virus (AAV)-based vector. Single chain and double chain AAV-based vectors have been developed that can be used for prolonged expression of small antisense nucleotide sequences for highly efficient skipping of the aberrant 128 nucleotide CEP290 exon.

A preferred AAV-based vector for instance comprises an expression cassette that is driven by a polymerase III-promoter (Pol III). A preferred Pol III promoter is, for example, a U1, a U6, or a U7 RNA promoter.

The invention therefore also provides a viral-based vector, comprising a Poi III-promoter driven expression cassette for expression of an antisense oligonucleotide of the invention for inducing skipping of aberrant 128 nucleotide CEP290 exon.

An AAV vector according to the present invention is a recombinant AAV vector and refers to an AAV vector comprising part of an AAV genome comprising an encoded exon skipping molecule according to the invention encapsidated in a protein shell of capsid protein derived from an AAV serotype as depicted elsewhere herein. Part of an AAV genome may contain the inverted terminal repeats (ITR) derived from an adeno-associated virus serotype, such as AAV1, AAV2, AAV3, AAV4, AAV5, AAV8, AAV9 and others. Protein shell comprised of capsid protein may be derived from an AAV serotype such as AAV1, 2, 3, 4, 5, 8, 9 and others. A protein shell may also be named a capsid protein shell. AAV vector may have one or preferably all wild type AAV genes deleted, but may still comprise functional ITR nucleic acid sequences. Functional ITR sequences are necessary for the replication, rescue and packaging of AAV virions. The ITR sequences may be wild type sequences or may have at least 80%, 85%, 90%, 95, or 100% sequence identity with wild type sequences or may be altered by for example in insertion, mutation, deletion or substitution of nucleotides, as long as they remain functional. In this context, functionality refers to the ability to direct packaging of the genome into the capsid shell and then allow for expression in the host cell to be infected or target cell. In the context of the present invention a capsid protein shell may be of a different serotype than the AAV vector genome ITR. An AAV vector according to present the invention may thus be composed of a capsid protein shell, i.e. the icosahedral capsid, which comprises capsid proteins (VP1, VP2, and/or VP3) of one AAV serotype, e.g. AAV serotype 2, whereas the ITRs sequences contained in that AAV5 vector may be any of the AAV serotypes described above, including an AAV2 vector. An "AAV2 vector" thus comprises a capsid protein shell of AAV serotype 2, while e.g. an "AAV5 vector" comprises a capsid protein shell of AAV serotype 5, whereby either may encapsidate any AAV vector genome ITR according to the invention.

Preferably, a recombinant AAV vector according to the present invention comprises a capsid protein shell of AAV serotype 2, 5, 8 or AAV serotype 9 wherein the AAV genome or ITRs present in said AAV vector are derived from AAV serotype 2, 5, 8 or AAV serotype 9; such AAV vector is referred to as an AAV2/2, AAV 2/5, AAV2/8, AAV2/9, AAV5/2, AAV5/5, AAV5/8, AAV 5/9, AAV8/2, AAV 8/5, AAV8/8, AAV8/9, AAV9/2, AAV9/5, AAV9/8, or an AAV9/9 vector.

More preferably, a recombinant AAV vector according to the present invention comprises a capsid protein shell of AAV serotype 2 and the AAV genome or ITRs present in said vector are derived from AAV serotype 5; such vector is referred to as an AAV 2/5 vector.

More preferably, a recombinant AAV vector according to the present invention comprises a capsid protein shell of AAV serotype 2 and the AAV genome or ITRs present in said vector are derived from AAV serotype 8; such vector is referred to as an AAV 2/8 vector.

More preferably, a recombinant AAV vector according to the present invention comprises a capsid protein shell of AAV serotype 2 and the AAV genome or ITRs present in said vector are derived from AAV serotype 9; such vector is referred to as an AAV 2/9 vector.

More preferably, a recombinant AAV vector according to the present invention comprises a capsid protein shell of AAV serotype 2 and the AAV genome or ITRs present in said vector are derived from AAV serotype 2; such vector is referred to as an AAV 2/2 vector.

A nucleic acid molecule encoding an exon skipping molecule according to the present invention represented by a nucleic acid sequence of choice is preferably inserted between the AAV genome or ITR sequences as identified above, for example an expression construct comprising an expression regulatory element operably linked to a coding sequence and a 3' termination sequence.

"AAV helper functions" generally refers to the corresponding AAV functions required for AAV replication and packaging supplied to the AAV vector in trans. AAV helper functions complement the AAV functions which are missing in the AAV vector, but they lack AAV ITRs (which are provided by the AAV vector genome). AAV helper functions include the two major ORFs of AAV, namely the rep coding region and the cap coding region or functional substantially identical sequences thereof. Rep and Cap regions are well known in the art, see e.g. Chiorini et al. (1999, J. of Virology, Vol 73(2): 1309-1319) or U.S. Pat. No. 5,139,941, incorporated herein by reference. The AAV helper functions can be supplied on a AAV helper construct, which may be a plasmid. Introduction of the helper construct into the host cell can occur e.g. by transformation, transfection, or transduction prior to or concurrently with the introduction of the AAV genome present in the AAV vector as identified herein. The AAV helper constructs of the invention may thus be chosen such that they produce the desired combination of serotypes for the AAV vector's capsid protein shell on the one hand and for the AAV genome present in said AAV vector replication and packaging on the other hand.

"AAV helper virus" provides additional functions required for AAV replication and packaging. Suitable AAV helper viruses include adenoviruses, herpes simplex viruses (such as HSV types 1 and 2) and vaccinia viruses. The additional functions provided by the helper virus can also be introduced into the host cell via vectors, as described in U.S. Pat. No. 6,531,456 incorporated herein by reference.

Preferably, an AAV genome as present in a recombinant AAV vector according to the present invention does not comprise any nucleotide sequences encoding viral proteins, such as the rep (replication) or cap (capsid) genes of AAV. An AAV genome may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art.

A preferred AAV vector according to the present invention is an AAV vector, preferably an AAV2/5, AAV2/8, AAV2/9 or AAV2/2 vector, expressing an exon skipping molecule according to the present invention comprising an antisense oligonucleotide, wherein said antisense oligonucleotide comprises or consists of a sequence selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9, SEQ ID NO: 10, SEQ ID NO 11, or SEQ ID NO: 12.

Improvements in means for providing an individual or a cell, tissue, organ of said individual with an exon skipping molecule according to the invention, are anticipated considering the progress that has already thus far been achieved. Such future improvements may of course be incorporated to achieve the mentioned effect on restructuring of mRNA using a method of the invention. An exon skipping molecule according to the invention can be delivered as is to art individual, a cell, tissue or organ of said individual. When administering an exon skipping molecule according to the invention, it is preferred that the molecule is dissolved in a solution that is compatible with the delivery method. Retina cells can be provided with a plasmid for antisense oligonucleotide expression by providing the plasmid in an aqueous solution. Alternatively, a plasmid can be provided by transfection using known transfection agents. For intravenous, subcutaneous, intramuscular, intrathecal and/or intraventricular administration it is preferred that the solution is a physiological salt solution. Particularly preferred in the invention is the use of an excipient or transfection agents that will aid in delivery of each of the constituents as defined herein to a cell and/or into a cell, preferably a retina cell. Preferred are excipients or transfection agents capable of forming complexes, nanoparticles, micelles, vesicles and/or liposomes that deliver each constituent as defined herein, complexed or trapped in a vesicle or liposome through a cell membrane. Many of these excipients are known in the art. Suitable excipients or transfection agents comprise polyethylenimine (PEI; ExGen500 (MBI Fermentas)), LipofectAMINE™ 2000 (Invitrogen) or derivatives thereof, or similar cationic polymers, including polypropyleneimine or polyethylenimine copolymers (PECs) and derivatives, synthetic amphiphils (SAINT-18), Lipofectin™, DOTAP and/or viral capsid proteins that are capable of self assembly into particles that can deliver each constitutent as defined herein to a cell, preferably a retina cell. Such excipients have been shown to efficiently deliver an oligonucleotide such as antisense nucleic acids to a wide variety of cultured cells, including retina cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent as defined herein, preferably an oligonucleotide, across cell membranes into cells.

In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an oligonucleotide. The skilled person may select and adapt any of the above or other commercially available alternative excipients and delivery systems to package and deliver an exon skipping molecule for use in the current invention to deliver it for the prevention, treatment or delay of a CEP290 related disease or condition. "Prevention, treatment or delay of a CEP290 related disease or condition" is herein preferably defined as preventing, halting, ceasing the progression of, or reversing partial or complete visual impairment or blindness that is caused by a genetic defect in the CEP290 gene.

In addition, an exon skipping molecule according to the invention could be covalently or non-covalently linked to a targeting ligand specifically designed to facilitate the uptake into the cell, cytoplasm and/or its nucleus. Such ligand could comprise (i) a compound (including but not limited to peptide(-like) structures) recognising cell, tissue or organ specific elements facilitating cellular uptake and/or (ii) a chemical compound able to facilitate the uptake in to cells and/or the intracellular release of an oligonucleotide from vesicles, e.g. endosomes or lysosomes.

Therefore, in a preferred embodiment, an exon skipping molecule according to the invention is formulated in a composition or a medicament or a composition, which is provided with at least an excipient and/or a targeting ligand for delivery and/or a delivery device thereof to a cell and/or enhancing its intracellular delivery.

It is to be understood that if a composition comprises an additional constituent such as an adjunct compound as later defined herein, each constituent of the composition may not be formulated in one single combination or composition or preparation. Depending on their identity, the skilled person will know which type of formulation is the most appropriate for each constituent as defined herein. In a preferred embodiment, the invention provides a composition or a preparation which is in the form of a kit of parts comprising an exon skipping molecule according to the invention and a further adjunct compound as later defined herein.

If required, an exon skipping molecule according to the invention or a vector, preferably a viral vector, expressing an exon skipping molecule according to the invention can be incorporated into a pharmaceutically active mixture by adding a pharmaceutically acceptable carrier.

Accordingly, the invention also provides a composition, preferably a pharmaceutical composition, comprising an exon skipping molecule according to the invention, or a viral vector according to the invention and a pharmaceutically acceptable excipient. Such composition may comprise a single exon skipping molecule according to the invention, but may also comprise multiple, distinct exon skipping molecules according to the invention. Such a pharmaceutical composition may comprise any pharmaceutically acceptable excipient, including a carrier, filler, preservative, adjuvant, solubilizer and/or diluent. Such pharmaceutically acceptable carrier, filler, preservative, adjuvant, solubilizer and/or diluent may for instance be found in Remington, 2000. Each feature of said composition has earlier been defined herein.

If multiple distinct exon skipping molecules according to the invention are used, concentration or dose defined herein may refer to the total concentration or dose of all oligonucleotides used or the concentration or dose of each exon skipping molecule used or added. Therefore in one embodiment, there is provided a composition wherein each or the total amount of exon skipping molecules according to the invention used is dosed in an amount ranged from 0.0001 and 20 mg/kg, preferably from 0.01 and 20 mg/kg.

A preferred exon skipping molecule according to the invention, is for the treatment of a CEP290 related disease or condition of an individual. In all embodiments of the present invention, the term "treatment" is understood to include the prevention and/or delay of the CEP290 related disease or condition. An individual, which may be treated using an exon skipping molecule according to the invention may already have been diagnosed as having a CEP290 related disease or condition. Alternatively, an individual which may be treated using an exon skipping molecule according to the invention may not have yet been diagnosed as having a CEP290 related disease or condition but may be an individual having an increased risk of developing a CEP290 related disease or condition in the future given his or her genetic background. A preferred individual is a human being. In a preferred embodiment the CEP290 related disease or condition is Leber congenital amaurosis.

Accordingly, the present invention further provides an exon skipping molecule according to the invention, or a viral vector according to the invention, or a composition according to the invention for use as a medicament, for treating a CEP290 related disease or condition requiring modulating splicing of CEP290 and for use as a medicament for the prevention, treatment or delay of a CEP290 related disease or condition. A preferred CEP290 related disease or condition is Leber congenital amaurosis. Each feature of said use has earlier been defined herein.

The invention further provides the use of an exon skipping molecule according to the invention, or of a viral vector according to the invention, or a composition according to the invention for the treatment of a CEP290 related disease or condition requiring modulating splicing of CEP290. In a preferred embodiment the CEP290 related disease or condition is Leber congenital amaurosis.

The present invention further provides an exon skipping molecule according to the invention, or of a viral vector according to the invention, or a composition according to the invention for the use as a medicine.

The invention further provides a method for treating a human carrying in its genome a mutation in intron 26 of the CEP290 gene (c. 2991+1655A>G), comprising administering to the human an AON, a viral vector, or a pharmaceutical composition of the invention. These patients can suffer from Leber congenital amaurosis.

Further embodiments of the invention are AONs, viral vectors encoding AONs, and pharmaceutical compositions comprising AONs according to the invention for use as a medicine to treat a human carrying in its genome a mutation in intron 26 of the CEP290 gene (c. 2991+1655A>G).

According to a further embodiment of the invention an in vitro and/or ex vivo method is provided for modulating splicing of CEP290 in a cell, said method comprising contacting said cell with an oligonucleotide, a viral vector encoding an oligonucleotide, or a pharmaceutical composition according to the invention.

Exon skipping molecules according to the invention may be administered to a patient systemically, locally, topically, through administration that is orally, intraocularly, intrapulmonary, intranasally, intramuscularly, subcutaneously, intradermally, rectally, by swallowing, injecting, inhalation, infusion, spraying, in the form of (aqueous) solutions, suspensions, (oil-in-water) emulsions, ointments, lozenges, pills etcetera. A preferred route of administration is through intra-vitreal injection of an aqueous solution or specially adapted formulation for intraocular administration. For example, EP-2,425,814 discloses an oil-in-water emulsion especially adapted for intraocular (intravitreal) administration of peptide or nucleic acid drugs. This emulsion is less dense than the vitreous fluid so it floats on top of the vitreous, avoiding that the injected drug impairs vision.

Dosing may be daily, weekly, monthly, quarterly, once per year, depending on the route of administration and the need of the patient.

Because of the early onset of disease, patients having LCA or at risk of developing the symptoms of LCA, including childhood blindness, may be treated in utero, directly after birth, from 1, 2, 3, 6 months of age, from one year of age, from 3 years of age, from 5 years of age, prior to or after the onset of symptoms, to alleviate, retard development, stop or reverse the symptoms of disease and the like.

A treatment in a use or in a method according to the invention is at least one week, at least one month, at least several months, at least one year, at least 2, 3, 4, 5, 6 years or during a patients entire life. Each exon skipping molecule or exon skipping oligonucleotide or equivalent thereof as defined herein for use according to the invention may be suitable for direct administration to a cell, tissue and/or an organ in vivo of individuals already affected or at risk of developing CEP290 related disease or condition, and may be administered directly in vivo, ex vivo or in vitro. The frequency of administration of an oligonucleotide, composition, compound or adjunct compound of the invention may depend on several parameters such as the age of the patient, the nature of the exon skipping molecule (e.g. gymnotic AON or vectored AON, such as AAV or lentiviral vector expressed AONs), the dose, the formulation of said molecule and the like.

Dose ranges of an exon skipping molecule, preferably an oligonucleotide according to the invention are preferably designed on the basis of rising dose studies in clinical trials (in vivo use) for which rigorous protocol requirements exist. An oligonucleotide as defined herein may be used at a dose range from 0.0001 to 20 mg/kg, preferably from 0.001 to 20 mg/kg. The dose and treatment regime may vary widely, depending on many factors, including but not limited to the route of administration (e.g. systemic versus topically, such as directly into the eye), whether the oligo is administered as a gymnotic AON or as vectored AON, the dosing regimen, the age and weight of the patient, and so forth.

In a preferred embodiment, a viral vector, preferably an AAV vector as described earlier herein, as delivery vehicle for a molecule according to the invention, is administered in a dose ranging from $1\times10^9$ $1\times10^{17}$ virus particles per injection, more preferably from $1\times10^{10}$ $1\times10^{14}$, and most preferably $1\times10^{10}$ $1\times10^{12}$ virus particles per injection.

It will be clear to a person having ordinary skill in the art to which this invention pertains, that the details of treatment will need to be established in accordance with and depending on such factors as the sequence and chemistry of the oligonucleotide(s), the route of administration, the formulation, the dose, the dosing regimen, the format (viral vector or gymnotic oligonucleotide), the age and weight of the patient, the stage of the disease and so forth, which may require further non-clinical and clinical investigation.

The invention further provides a method for modulating splicing of CEP290 in a cell comprising contacting the cell, preferably a retina cell, with an exon skipping molecule according to the invention, or a viral vector according to the invention, or a composition according to the invention. The features of this aspect are preferably those defined earlier herein. Contacting the cell with an exon skipping molecule according to the invention, or a viral vector according to the invention, or a composition according to the invention may be performed by any method known by the person skilled in the art. Use of the methods for delivery of exon skipping molecules, viral vectors and compositions described herein is included. Contacting may be directly or indirectly and may be in vivo, ex vivo or in vitro.

Unless otherwise indicated each embodiment as described herein may be combined with another embodiment as described herein.

The ability of an oligonucleotide to reduce splice site selection of an aberrant splice site associated with the c.29914-1655A>G mutation in intron 26 of the human CEP290 gene when said gene is expressed in a human cell, and to bind to the human CEP290 pre-mRNA under physiological conditions in a region affecting selection of the aberrant splice site and thereby reduce selection of the aberrant splice site by the cell's splicing machinery, can be conveniently assessed using the assays disclosed in the experimental section herein. In particular, the oligo can be incubated with a cell containing the c.2991+1655A>G mutation and its ability to reduce production by the cell of mRNA which includes the aberrant exon can be assessed e.g. by RT-PCR.

As can be observed in the experimental section herein, at the RNA level, addition of various AONs targeting the aberrant CEP290 exon indeed resulted in a conversion of aberrantly spliced CEP290 mRNA to correctly spliced CEP290 mRNA. This conversion will coincide with an increased synthesis of the wild-type CEP290 protein.

In fibroblasts (that can be derived from skin cells), CEP290 is abundantly expressed. Therefore, it is to be expected that addition of AONs to cultured fibroblasts from LCA patients will result in an increased amount of wild-type CEP290 protein that is detectable on Western blot, and as such will demonstrate that AON-based therapy will not only redirect normal splicing of CEP290 mRNA but will also result in restoring CEP290 protein function.

The terms "adenine", "guanine", "cytosine", "thymine", "uracil" and hypoxanthine (the nucleobase in inosine) refer to the nucleobases as such.

The terms adenosine, guanosine, cytidine, thymidine, uridine and inosine, refer to the nucleobases linked to the (desoxy)ribosyl sugar.

The term "nucleoside" refers to the nucleobase linked to the (deoxy)ribosyl sugar.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) plus or minus 5% of the value.

The sequence information as provided herein should not be so narrowly construed as to require inclusion of erroneously identified bases. The skilled person is capable of identifying such erroneously identified bases and knows how to correct for such errors. In case of sequence errors, the sequence of the polypeptide obtainable by expression of the gene present in SEQ ID NO: 1 containing the nucleic acid sequence coding for the polypeptide should prevail.

Materials and Methods

1: Cells

All cell lines are human fibroblasts, generated from skin biopsies. LFB1 (CL10-00008) and LFB2 (CL12-00027) are wild type and represent control cell lines, LFB3 (CL12-00035) and LFB4 (CL12-00036) are both homozygous mutant for a mutation in CEP290 (c.2991+1655A>G).

2: AONs

AONs were designed using a "genewalk" approach, where 17mer AONs were design to cover the cryptic 128 bp exon, with an overlapping region between AONs of approximately 10 bp. The designed RNA AONs, with 2'-O-methylphosphorothioate chemistry, were obtained from Integrated DNA Technologies (IDT).

3: Cell Culture and Transfection

All cell lines were grown in DMEM-AQE medium (Sigma) supplemented with 20% FBS, and 1% sodium pyruvate. A day before transfection, cells were seeded in a density of $2\times10^5$/well on a 6-well plate in a total volume of 2.5 ml of medium. The day of the transfection, the AON to be tested was added to each well in a final concentration of 100 nM using maxPEI (Poliscience) as a transfection agent (all in PBS), with a mass ratio oligo:maxPEI of 1:4. After 24 h, cells are washed with PBS and cell lysate was collected using the BL+TG buffer supplied with the ReliaPrep RNA Cell Miniprep System kit (Promega). Cell lysates were frozen at −80° C. until further use.

4: Profiling of Wt and Mt CEP290 in Samples a) RNA Isolation: RNA was isolated, from the cell lysates that had been kept at −80° C., using the ReliaPrep RNA Cell Miniprep System kit (Promega) according to the manufacturer's protocol. Total RNA was quantified using a Nanodrop 2000 spectrophotometer (Nanodrop Technologies) before storing it at −80° C.

b) cDNA synthesis: 400 ng of RNA was used as template for the cDNA synthesis using the Verso cDNA synthesis kit (Thermoscientific) with oligodT primers according to the manufacturer's instructions. A non-RT sample (without the enzyme) was included as control and was analyzed along with the rest of the samples.

c) PCR: to visualize and quantify the different profiles of messenger RNA of CEP290 present in the samples, a fragment of CEP290 mRNA, encompassing exon26 to exon27, was specifically amplified using PCR. For this purpose, the cDNA (2 µl of a dilution 2.5×) was used as template and amplification of the target sequence was done using the following primers:

```
                                         (SEQ ID NO: 23)
ex26_Fw: 5'-TGCTAAGTACAGGGACATCTTGC-3'

(SEQ ID NO: 24)
ex27_Rv: 5'-AGACTCCACTTGTTCTTTTAAGGAG-3'.
```

The reaction was carried out using AmpliTaq Gold® 360 DNA Polymerase (Life technologies; Cat. No: 4398833).

| PCR program | | | |
|---|---|---|---|
| hold | 5 min | 95° C. | |
| denature | 30 sec | 95° C. | |
| anneal | 30 sec | 58° C. | 35 cycles |
| extend | 35 sec | 72° C. | |
| final | | | |
| extension | 7 min | 72° C. | |
| hold | infinite | 4° C. | |

PCR fragments were analyzed using the Bioanalyzer 2100 (DNA 1000 kit, Agilent Technologies). Results were analyzed using the 2100 Expert software (Agilent Technologies).

d) RT-qPCR: to measure the level of expression of CEP290 messenger RNA, wild type and mutant transcripts were amplified as 93 bp and 117 bp fragments, respectively. The human P0 large ribosomal protein mRNA (RPLP0) was used for normalization. For this, cDNAs (2 ul of a 10× dilution) were amplified in a qPCR buffer (18 ul) containing SYBR select master mix (Life Technologies) and 400 nM of forward and reverse primers (SEQ ID NOs 25-28). The system used for amplification was a CFX96 Real-Time PCR Detection system (Biorad) and the conditions were as follows: an UDG activation step at 50° C. for 2 min, next a first denaturation step at 95° C. for 2 min followed by 50 cycles of 95° C. for 15 seconds and 62.5° C. for 1 min. A melting curve analysis was performed at the end of each run to determine the specificity of the amplification products. Data was visualized and processed using the Bio-rad software and the fold change calculations were performed using the Comparative Ct method (also known as the 2(-Delta Delta C(T)) method).

The primers used are:

```
                                            (SEQ ID NO: 25)
    wt_Fw: 5'-TGACTGCTAAGTACAGGGACATCTTG-3'

(SEQ ID NO: 26)
    wt-Rv: 5'-AGGAGATGTTTTCACACTCCAGGT-3'

(SEQ ID NO: 27)
    mt_Fw: 5'-CTGGCCCCAGTTGTAATTTGTGA-3'

(SEQ ID NO: 28)
    mt_Rv: 5'-CTGTTCCCAGGCTTGTTCAATAGT-3'
```

For this reaction, SYBR select master mix (Life Technologies) along with cDNA diluted 10× used as template.

Results and Discussion

Effects on RNA modulation of the designed oligonucleotides were assessed after optimization for transfection efficiency and treatment time and concentration (data not shown).

Efficiency of exon skipping induced by the designed $2^3$-O-methyl-phosphorothioate AONs, was screened using the selected amplification of a CEP290 fragment, encompassing exon26 to exon27. Visualization and quantification of the PCR fragments was performed using a Bioanalyzer 2100. We asked ourselves whether it would be possible to design AONs that induce exon skipping—as established by determining the levels of the PCR fragment corresponding to the mutated spliced mRNA compared to the wt spliced mRNA with equivalent or better efficiency than AONs described in the prior art, while being devoid of structures that would hamper their manufacture or therapeutic use. This work identified 11 oligonucleotides which meet these criteria (see FIG. 2, Table 1 and Table 2).

Analysis of the level of expression of wild type and mutant transcripts of CEP290 messenger RNA through qPCR confirmed the results obtained with the Bioanalyzer 2100. Fold change calculations show that treatment with antisense oligonucleotides of the invention rescues expression of wild type transcripts to levels equal to or superior of those achieved by the AONs described in the previous art.

As it is not a requirement that the AONs of the invention perform better in terms of exon skipping than those of the prior art, sufficient performance to induce exon skipping is enough. The AONs according to the invention disclosed in the examples are just preferred embodiments of the invention. Other AONs that fulfill the requirements of the invention as claimed can be designed that are encompassed by the present invention.

TABLE 1 quantification (ng/µl) of mRNA profiles in patient samples using the Bioanalyzer 2100

|  | NT | SON-3 | AON-3 | ESE (+50 + 70) | AONP 2 | AONP 3 | AONP 4 | AONP 11 | AONP 12 | AONP 13 | AONP 19 | AONP 20 | AONP 23 | AONP 24 | AONP 26 |
|---|---|---|---|---|---|---|---|---|---|---|---|---|---|---|---|
| WT band | 8.2 | 7.72 | 11.2 | 9.3 | 8.9 | 12.12 | 12.76 | 11.01 | 10.07 | 11.72 | 10.32 | 10.75 | 13.56 | 11.09 | 13.9 |
| MT band | 1.62 | 3.13 | 0.09 | 0.22 | 0.11 | 0.08 | 0.06 | 0.06 | 0.1 | 0.07 | 0.04 | 0.05 | 0.21 | 0.15 | 0.16 |
| extra band 1 | 0.2 | 0.48 | 0 | 0.05 | 0 | 0 | 0 | 0 | 0.01 | 0 | 0.02 | 0 | 0.02 | 0.02 | 0 |
| extra band 2 | 0.19 | 0.45 | 0 | 0.06 | 0 | 0 | 0 | 0 | 0.01 | 0 | 0.02 | 0 | 0.02 | 0.02 | 0.02 |
| Total | 10.21 | 11.78 | 11.29 | 9.63 | 9.01 | 12.2 | 12.82 | 11.07 | 10.19 | 11.79 | 10.4 | 10.8 | 13.81 | 11.28 | 14.08 |

MT = mutant band; band1 and band2 are apparent by-products of aberrant splicing
SON-3 = cgcaccuggcccaguu (SEQ ID NO: 29, previously disclosed in WO2013/036105 and by Collin et al., 2012).

TABLE 2 relative amounts (%) of CEP290 mRNA profiles non-treated patient cells (NT), patient cells treated with non-complementary (sense) oligonucleotide (SON-3) or complementary antisense oligonucleotides according to the invention (AONP) compared to prior art AONs

|  | NT | SON-3 | AON-3 | ESE (+50 + 70) | AONP 2 | AONP 3 | AONP 4 | AONP 11 | AONP 12 | AONP 13 | AONP 19 | AONP 20 | AONP 23 | AONP 24 | AONP 26 |
|---|---|---|---|---|---|---|---|---|---|---|---|---|---|---|---|
| WT band | 80.31 | 65.53 | 99.20 | 96.57 | 98.78 | 99.34 | 99.53 | 99.46 | 98.82 | 99.41 | 99.23 | 99.54 | 98.19 | 98.32 | 98.72 |
| MT band | 15.87 | 26.57 | 0.80 | 2.28 | 1.22 | 0.66 | 0.47 | 0.54 | 0.98 | 0.59 | 0.38 | 0.46 | 1.52 | 1.33 | 1.14 |
| extra band 1 | 1.96 | 4.07 | 0.00 | 0.52 | 0.00 | 0.00 | 0.00 | 0.00 | 0.10 | 0.00 | 0.19 | 0.00 | 0.14 | 0.18 | 0.00 |
| extra band 2 | 1.86 | 3.82 | 0.00 | 0.62 | 0.00 | 0.00 | 0.00 | 0.00 | 0.10 | 0.00 | 0.19 | 0.00 | 0.14 | 0.18 | 0.14 |

The invention claimed is:

1. An oligonucleotide capable of reducing splice site selection of an aberrant splice site associated with the c.2991+1655A>G mutation in intron 26 of the human CEP290 gene, when said gene is expressed in a human cell, characterized in that the oligonucleotide's sequence consists of the sequence of SEQ ID NO: 7, wherein i) all ribose moieties of the oligonucleotide are 2'-O-methyl modified, and
ii) all internucleosidic linkages of the oligonucleotide are phosphorothioate linkages.

2. A pharmaceutical composition comprising an oligonucleotide according to claim 1.

* * * * *

SEQUENCE LISTING

<160> NUMBER OF SEQ ID NOS: 36

<210> SEQ ID NO 1
<211> LENGTH: 128
<212> TYPE: DNA
<213> ORGANISM: Homo sapiens

<400> SEQUENCE: 1
tagagatggg gtttcacctt gttagccagg atggtgtcga tctcctgaac tcgtgatcca      60
cccgcctcgg cctcctaaag tgctgggatt acagatgtga gccaccgcac ctggccccag     120
ttgtaatt                                                              128

<210> SEQ ID NO 2
<211> LENGTH: 17
<212> TYPE: RNA
<213> ORGANISM: Artificial Sequence
<220> FEATURE:
<223> OTHER INFORMATION: Antisense oligonucleotide

<400> SEQUENCE: 2
gcgguggcuc acaucug                                                     17

<210> SEQ ID NO 3
<211> LENGTH: 17
<212> TYPE: RNA
<213> ORGANISM: Artificial Sequence
<220> FEATURE:
<223> OTHER INFORMATION: Antisense oligonucleotide

<400> SEQUENCE: 3
gguggcucac aucugua                                                     17

<210> SEQ ID NO 4
<211> LENGTH: 17
<212> TYPE: RNA
<213> ORGANISM: Artificial Sequence
<220> FEATURE:
<223> OTHER INFORMATION: Antisense oligonucleotide

<400> SEQUENCE: 4
ggcucacauc uguaauc                                                     17

<210> SEQ ID NO 5
<211> LENGTH: 17
<212> TYPE: RNA
<213> ORGANISM: Artificial Sequence
<220> FEATURE:
<223> OTHER INFORMATION: Antisense oligonucleotide

<400> SEQUENCE: 5
ucaggagauc gacacca                                                     17

<210> SEQ ID NO 6
<211> LENGTH: 17
<212> TYPE: RNA
<213> ORGANISM: Artificial Sequence
<220> FEATURE:
<223> OTHER INFORMATION: Antisense oligonucleotide

<400> SEQUENCE: 6
cacgaguuca ggagauc                                                     17

<210> SEQ ID NO 7
<211> LENGTH: 17

```
<212> TYPE: RNA
<213> ORGANISM: Artificial Sequence
<220> FEATURE:
<223> OTHER INFORMATION: Antisense oligonucleotide

<400> SEQUENCE: 7
gguggaucac gaguuca                                                    17

<210> SEQ ID NO 8
<211> LENGTH: 17
<212> TYPE: RNA
<213> ORGANISM: Artificial Sequence
<220> FEATURE:
<223> OTHER INFORMATION: Antisense oligonucleotide

<400> SEQUENCE: 8
uggcucacau cuguaau                                                    17

<210> SEQ ID NO 9
<211> LENGTH: 17
<212> TYPE: RNA
<213> ORGANISM: Artificial Sequence
<220> FEATURE:
<223> OTHER INFORMATION: Antisense oligonucleotide

<400> SEQUENCE: 9
ugcgguggcu cacaucu                                                    17

<210> SEQ ID NO 10
<211> LENGTH: 17
<212> TYPE: RNA
<213> ORGANISM: Artificial Sequence
<220> FEATURE:
<223> OTHER INFORMATION: Antisense oligonucleotide

<400> SEQUENCE: 10
cucacaauua caacugg                                                    17

<210> SEQ ID NO 11
<211> LENGTH: 17
<212> TYPE: RNA
<213> ORGANISM: Artificial Sequence
<220> FEATURE:
<223> OTHER INFORMATION: Antisense oligonucleotide

<400> SEQUENCE: 11
gguaugagau acucaca                                                    17

<210> SEQ ID NO 12
<211> LENGTH: 17
<212> TYPE: RNA
<213> ORGANISM: Artificial Sequence
<220> FEATURE:
<223> OTHER INFORMATION: Antisense oligonucleotide

<400> SEQUENCE: 12
ggauagguau gagauac                                                    17

<210> SEQ ID NO 13
<211> LENGTH: 31
<212> TYPE: RNA
<213> ORGANISM: Artificial Sequence
<220> FEATURE:
<223> OTHER INFORMATION: Antisense oligonucleotide

<400> SEQUENCE: 13
```
cuggggccag gugcgguggc ucacaucugu a          31

<210> SEQ ID NO 14
<211> LENGTH: 25
<212> TYPE: RNA
<213> ORGANISM: Artificial Sequence
<220> FEATURE:
<223> OTHER INFORMATION: Antisense oligonucleotide

<400> SEQUENCE: 14
gggauaggua ugagauacuc acaau          25

<210> SEQ ID NO 15
<211> LENGTH: 21
<212> TYPE: RNA
<213> ORGANISM: Artificial Sequence
<220> FEATURE:
<223> OTHER INFORMATION: Antisense oligonucleotide

<400> SEQUENCE: 15
ccgaggcggg uggaucacga g          21

<210> SEQ ID NO 16
<211> LENGTH: 22
<212> TYPE: RNA
<213> ORGANISM: Artificial Sequence
<220> FEATURE:
<223> OTHER INFORMATION: Antisense oligonucleotide

<400> SEQUENCE: 16
gguaugagau acucacaauu ac          22

<210> SEQ ID NO 17
<211> LENGTH: 31
<212> TYPE: RNA
<213> ORGANISM: Artificial Sequence
<220> FEATURE:
<223> OTHER INFORMATION: Antisense oligonucleotide

<400> SEQUENCE: 17
gguaugagau acucacaauu acaacugggg c          31

<210> SEQ ID NO 18
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 18
taatcccagc actttaggag          20

<210> SEQ ID NO 19
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 19
gggccaggtg cggtgg          16

<210> SEQ ID NO 20
<211> LENGTH: 17
<212> TYPE: DNA
<213> ORGANISM: Artificial Sequence

```
<220> FEATURE:
<223> OTHER INFORMATION: Antisense oligonucleotide

<400> SEQUENCE: 20
aactggggcc aggtgcg                                                    17

<210> SEQ ID NO 21
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 21
tacaactggg gccaggtg                                                   18

<210> SEQ ID NO 22
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 22
actcacaatt acaactgggg                                                 20

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
tgctaagtac agggacatct tgc                                             23

<210> SEQ ID NO 24
<211> LENGTH: 25
<212> TYPE: DNA
<213> ORGANISM: Artificial Sequence
<220> FEATURE:
<223> OTHER INFORMATION: primer

<400> SEQUENCE: 24
agactccact tgttctttta aggag                                           25

<210> SEQ ID NO 25
<211> LENGTH: 26
<212> TYPE: DNA
<213> ORGANISM: Artificial Sequence
<220> FEATURE:
<223> OTHER INFORMATION: primer

<400> SEQUENCE: 25
tgactgctaa gtacagggac atcttg                                          26

<210> SEQ ID NO 26
<211> LENGTH: 24
<212> TYPE: DNA
<213> ORGANISM: Artificial Sequence
<220> FEATURE:
<223> OTHER INFORMATION: primer

<400> SEQUENCE: 26
aggagatgtt ttcacactcc aggt                                            24
```

```
<210> SEQ ID NO 27
<211> LENGTH: 23
<212> TYPE: DNA
<213> ORGANISM: Artificial Sequence
<220> FEATURE:
<223> OTHER INFORMATION: primer

<400> SEQUENCE: 27
ctggccccag ttgtaatttg tga                                            23

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
ctgttcccag gcttgttcaa tagt                                           24

<210> SEQ ID NO 29
<211> LENGTH: 17
<212> TYPE: RNA
<213> ORGANISM: Artificial Sequence
<220> FEATURE:
<223> OTHER INFORMATION: Sense oligonucleotide

<400> SEQUENCE: 29
cgcaccuggc cccaguu                                                   17

<210> SEQ ID NO 30
<211> LENGTH: 158
<212> TYPE: DNA
<213> ORGANISM: Homo sapiens

<400> SEQUENCE: 30
tagagatggg gtttcacctt gttagccagg atggtgtcga tctcctgaac tcgtgatcca    60
cccgcctcgg cctcctaaag tgctgggatt acagatgtga gccaccgcac ctggccccag   120
ttgtaattgt gaatatctca tacctatccc tattggca                           158

<210> SEQ ID NO 31
<211> LENGTH: 26
<212> TYPE: DNA
<213> ORGANISM: Homo sapiens

<400> SEQUENCE: 31
atggtgtcga tctcctgaac tcgtga                                         26

<210> SEQ ID NO 32
<211> LENGTH: 8
<212> TYPE: DNA
<213> ORGANISM: Artificial Sequence
<220> FEATURE:
<223> OTHER INFORMATION: Homo sapiens

<400> SEQUENCE: 32 atctcctg                                                              8

<210> SEQ ID NO 33
<211> LENGTH: 22
<212> TYPE: RNA
<213> ORGANISM: Artificial Sequence
<220> FEATURE:
<223> OTHER INFORMATION: Micro RNA
```

```
<400> SEQUENCE: 33
gcgguggcuc acaucuguaa uc                                           22

<210> SEQ ID NO 34
<211> LENGTH: 23
<212> TYPE: RNA
<213> ORGANISM: Artificial Sequence
<220> FEATURE:
<223> OTHER INFORMATION: Micro RNA

<400> SEQUENCE: 34
gggcgcggug gcucacaucu gua                                          23

<210> SEQ ID NO 35
<211> LENGTH: 19
<212> TYPE: RNA
<213> ORGANISM: Artificial Sequence
<220> FEATURE:
<223> OTHER INFORMATION: siRNA

<400> SEQUENCE: 35
cgcgguggcu cacaucugu                                               19

<210> SEQ ID NO 36
<211> LENGTH: 8
<212> TYPE: DNA
<213> ORGANISM: Homo sapiens

<400> SEQUENCE: 36 caggagat                                                            8
```